United States Patent [19]

Wang

[11] Patent Number: 4,963,691

[45] Date of Patent: Oct. 16, 1990

[54] SPIRODILACTAM DERIVATIVES

[75] Inventor: Pen-Chung Wang, Houston, Tex.

[73] Assignee: Shell Oil Company, Houston, Tex.

[21] Appl. No.: 392,312

[22] Filed: Aug. 11, 1989

[51] Int. Cl.$^5$ ................. C07D 487/10; C08F 22/40
[52] U.S. Cl. .................................................. 548/410
[58] Field of Search ...................................... 548/410

[56] References Cited

U.S. PATENT DOCUMENTS

| | | | |
|---|---|---|---|
| 4,064,086 | 12/1977 | Cowsar | 260/29.2 R |
| 4,847,388 | 7/1989 | Wang | 548/410 |
| 4,885,351 | 12/1989 | Wang | 548/409 |
| 4,886,863 | 12/1989 | Wang | 548/409 |
| 4,888,408 | 12/1989 | Wang | 548/323 |

OTHER PUBLICATIONS

Pariza et al, Synthetic Communications, vol. 13(3) pp. 243–254 (1983).
Vanderbilt et al, "Biodegradable Polymers Based on 4,4'Spirobibutylrolactone", Abstract, p. 521, ACS Meeting, Sep. 1988, Los Angeles.
Overberger, Chem. Abs. 95, 42180a (1981).

Primary Examiner—Mark L. Berch

[57] ABSTRACT

Novel monomeric compounds containing the 2,7-diazaspiro[4.4]-nonane-1,6-dioine ring system are produced by contacting an amine hydrohalide and a 2,7-dioxaspiro[4.4]nonane-1,6-dione. The resulting spirodilactam compounds are characterized by improved hydrolytic and thermal oxidative stability.

6 Claims, No Drawings

SPIRODILACTAM DERIVATIVES

FIELD OF THE INVENTION

This invention relates to a novel class of spirodilactam derivatives. More particularly, the invention relates to 2,7diazapiro-[4.4]nonane-1,6-dione compounds having substituents on the spiro ring nitrogen atoms.

BACKGROUND OF THE INVENTION

The class of spirodilactones, as exemplified by 1,6-dioxospiro[4.4]-2,7-dione, has been known for a number of years. For example, see Pariza et al, Synthetic Communications, Vol. 13(3), pp. 243–254 (1983), and Cowsar et al, U.S. Pat. No. 4,064,086. Until recently, the corresponding classes of spirodilactams were unknown. Vanderbilt et al, "Biodegradable Polyamides Based on 4,4'-spirobibutyrolactone", Abstract, p. 521, ACS Meeting, Sept. 1988, Los Angeles, have described a polymeric system in which one monomeric unit has the 2,7-diazaspiro[4.4]nonane-3,8-dione ring system. No monomeric compounds are disclosed which incorporate this ring system. In a series of copending U.S. patent applications of which Serial No. 245,618, filed Sept. 16, 1988, is illustrative, monomeric compounds containing the 1,6-diazaspiro[4.4]nonane-2,7-dione are disclosed and claimed. By way of specific illustration, compounds such as 1,6-di(4-hydroxyphenyl)-1,6-diazaspiro[4.4]nonane-2,7-dione are prepared. This compound is useful as a precursor of polymeric materials, both thermoplastic and thermoset, which would contain the 1,6-diazapiro[4.4]nonane-2,7-dione ring system. Polymers containing the latter ring system, and presumably the ring system of Vanderbilt et al have many useful properties but in some applications demonstrate thermal oxidative instability and instability to water at elevated temperatures. Indeed, this is recognized by Vanderbilt et al who are seeking to find polymers for biomedical use which will biodegrade. For other applications, however, the thermal and water instability can be detrimental if polymers containing these spirodilactam ring systems are exposed to moisture or oxygen at elevated conditions.

Without wishing to be bound by any particular theory, whatever instability is observed is likely due to the presence within the molecule of active methylene hydrogen atoms which are alpha or adjacent to a carbonyl group. Any such difficulties of water or oxygen instability at elevated temperatures can be overcome by the substitution of the active methylene hydrogens with alkyl groups or other substituents. For example, there is disclosed in Ser. No. 245,618, filed Sept. 16, 1988, the production of compounds containing a 3,3,8,8-tetramethyl-1,6-diazspiro[4.4]nonane-2,7-dione ring system. Such ring substituted spirodilactams demonstrate greater thermal oxidative and hydrolytic stability at elevated temperatures. It would be of advantage, however, to provide a spirodilactam ring system which is free of active methylene carbon atoms and therefore demonstrates greater stability towards oxygen and moisture at elevated temperature.

SUMMARY OF THE INVENTION

The present invention provides a class of 2,7-diaza[4.4]spirodilactam derivatives of improved stability. More particularly, the present invention provides a novel class of 2,7-diazaspiro[4.4]nonane-1,6-dione compounds.

DESCRIPTION OF THE INVENTION

The compounds of the present invention are 2,7-diazaspiro[4.4]nonane-1,6-dione compounds. This ring system is shown by Smirnova et al, Zh. Org. Khim., 4(9), 1665–1670 (1968), but the possibility of nitrogen substituents is precluded by the method of synthesis. The compounds of the invention, however, have substituents on the spiro ring nitrogen atoms. Preferred members of this class have up to 60 carbon atoms and are represented by the formula

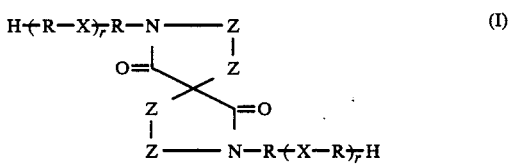

wherein Z independently is $>C(Z')_2$ in which Z' independently is hydrogen, alkyl, particularly lower alkyl of up to 4 carbon atoms inclusive, halo, particularly the lower halogens fluoro or chloro, or aryl, particularly phenyl. The above term R independently is aromatic or aliphatic of up to 10 carbon atoms and is hydrocarbyl containing only atoms of carbon and hydrogen or is substituted hydrocarbyl containing additional atoms such as halogen, preferably middle halogen chloro or bromo, in the form of monovalent substituents which are inert, at least under the conditions under which the spirodilactam compound is produced. The term X independently is a direct valence bond, alkylene of up to 8 carbon atoms inclusive, oxy thio, sulfonyl, carbonyl, dioxyphenylene, 2,2-di(oxyphenyl) propane, di(oxyphenyl) sulfone or dioxydiphenylene, and r independently is 0 or 1.

Compounds of the above formula I wherein the Z moieties are acyclic as not being part of a fused ring system, i.e., each Z is $>C(Z')_2$, are illustrated by 2,7-diphenyl-2,7-diazaspiro[4.4]nonane-1,6-dione, 3,8-dimethyl-2,7-diphenyl-2,7-diazaspiro[4.4]nonane-1,6-dione, 2,7-dibutyl-2,7-diazaspiro[4.4]-1,6-dione, 2,7-di(4-methoxyphenyl)-3,8-diphenyl-2,7-diazaspiro[4.4]nonane-1,6-dione, 2,7-di(4-phenylphenyl)-2,7-diazaspiro[4.4]-nonane-1,6-dione, 2,7-dioctyl-3,8-dichloro-2,7-diazaspiro[4.4]nonane-1,6-dione, 2,7-di(4-benzoylphenyl)-3,4,8,9-tetrafluoro-2,7-diazaspiro[4.4]nonane-1,6-dione and 2,7-dibenzyl-3,8-dibutyl-2,7-diazaspiro[4.4]nonane-1,6-dione.

The preferred spirodilactam compounds of the above formula are those wherein R is aromatic and further preferred are such spirodilactams wherein each r is 0. Within the spirodilactam ring system, the preferred spirodilactam compounds are those wherein each Z is $>C(Z')_2$ in which at least one Z' on each Z'-substituted carbon atom is Z' is hydrogen or lower alkyl, particularly hydrogen.

The production of the spirodilactams of the invention comprises reaction between an amine salt, preferably an amine hydrohalide and a spirodilactone corresponding to the structure of the spirodilactam whose production is desired. In terms of the preferred spirodilactams of formula I, the amine hydrohalide is a compound of up to 30 carbon atoms inclusive and is represented by the formula

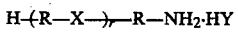 (II)

wherein R, X and r have the previously stated meanings and Y is halogen, e.g., fluorine, chlorine, bromine or iodine, but is preferably midde halogen chlorine or bromine. In the process of the invention the presence of the amine, or at least a substantial proportion of the amine, as the hydrohalide salt is required and in the absence of amine hydrohalide the desired reaction will not take place. Suitable amine hydrohalides of formula II include aniline hydrochloride, p-methoxyaniline hydrobromide, 4-aminobiphenyl hydroiodide, 4-aminodiphenyl sulfone hydrochloride, heptylamine hydrobromide and 2,4-dimethylaniline hydrochloride. Other amine hydrohalide precursors of the spirodilactams of the invention will be apparent from consideration of formula II and the components thereof.

The second reactant employed in the production of the spirodilactams of the invention are the corresponding spirodilactones. In terms of the spirodilactam products of formula I, the spirodilactone precursors are represented by the formula

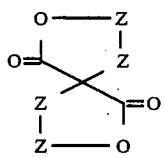 (III)

wherein Z has the previously stated meaning. Illustrative spirodilactone reactants of this formula III include 2,7-dioxaspiro[4.4]nonane-1,6-dione, 3,8-dimethyl-2,7-dioxaspiro[4.4]nonane-1,6-dione, 3,4,8,9-diethyl-2,7-dioxaspiro[4.4]nonane-1,6-dione, 4,9-diphenyl-2,7-dioxaspiro[4.4]nonane-1,6-dione and 3,4,8,9-dibenzo-2,7-dioxaspiro[4.4]nonane-1,6-dione. These spirodilactone reactants are known compounds or are prepared by known methods, e.g., *J. Org. Chem.*, 50, 1026 (1985).

The reaction of the amine hydrohalide and the spirodilactone is conducted under reaction conditions in a liquid phase in the presence of a reaction diluent. Preferred reaction diluents are polar reaction diluents and are illustrated by ethers including acyclic ethers such as diethylene glycol dimethyl ether and tetraethylene glycol dimethyl ether as well as cyclic ethers such as tetrahydrofuran and dioxane, sulfur containing diluents such as sulfolane and dimethyl sulfoxide and N-alkylamides such as N,N-dimethyformamide, N,N-dimethylacetamide and N-methyl-2-pyrrolidone. In a preferred modification, however, the polar reaction diluent is the amine corresponding to the amine hydrochloride reactant. The amine hydrohalide, the spirodilactone and the reaction diluent are charged to a suitable reactor and maintained under reaction conditions. Suitable reaction conditions include an elevated reaction temperature of from about 25° C. to about 250° C., preferably from about 100° C. to about 200° C. In a particularly useful procedure, the reaction mixture is maintained at the reflux temperature of the mixture. Typical reaction pressures are up to about 10 atmospheres but more often from about 0.8 atmosphere to about 5 atmospheres. During reaction, the contact of the reactants is maintained by conventional proceduress such as shaking, stirring or refluxing, and subsequent to reaction the desired 2,7-diaza [4.4]spirodilactam product is recovered from the product mixture by well known procedures such as distillation, diluent removal, precipitation or chromatographic methods.

The 2,7-diazaspiro[4.4]nonane-1,6-dione products of the invention are useful in a variety of applications where the absence of activated methylene hydrogen atoms imparts hydrolytic and thermal oxidative stability. When the substituents on the spiro ring nitrogen atoms are substituted hydrocarbyl, advantage can be taken of the substituent groups to facilitate incorporation of the spirodilactam moieties into a polymeric chain. For example, 2,7-di(4-chlorophenyl)-2,7-diazaspiro[4.4]nonane-1,6-dione is reacted with an alkali metal salt of a bisphenol to produce a polyether which will have good properties at elevated temperatures because of the presence of the polycyclic structures in the polymeric chain. When the substituents of the spiro ring nitrogen atoms are hydrocarbyl, the compounds are useful as an ultraviolet (UV) stabilizer or plasticizer.

The invention is further illustrated by the following Illustrative Embodiment which should not be regarded as limiting the invention.

ILLUSTRATIVE EMBODIMENT

A mixture of 53.6 g (0.02 mole) of 3,8-dibutyl-2,7-dioxospiro-[4.4]nonane-1,6-dione, 10.32 g (0.08 mole) of aniline hydrochloride and 40 ml of aniline was placed in a 500 ml round bottom flask and heated to reflux. After refluxing for 6 hours, the aniline was removed by distillation at reduced pressure. The resulting mixture was subjected to column chromatography employing a 2:1 mixture of diethyl ether and petroleum ether as eluent. The product, 3,8-dibutyl-2,7-diphenyl-2,7-diazaspiro[4.4]nonane-1,6-dione, was isolated as a viscous oil in a yield of about 86%. The infrared, $^{13}$C-NMR and mass spectra of the product were consistent with this structure.

What is claimed is:

1. A spirodilactam of the formula

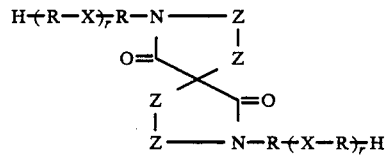

wherein Z independently is $>C(Z')_2$ in which Z' independently is hydrogen, lower alkyl, lower halo or phenyl, R independently is a phenylene group, X independently is a direct valence bond, alkylene of up to 8 carbon atoms inclusive, oxy, thio, sulfonyl, dioxyphenylene, 2,2-di(oxyphenyl)propane, di(oxyphenyl) sulfone or dioxydiphenylene, and r independently is 0 or 1.

2. The spirodilactam of claim 1 wherein each Z is $>C(Z')_2$ wherein Z' is hydrogen or lower alkyl.

3. The spirodilactam of claim 2 wherein each r is 0.

4. The spirodilactam of claim 3 wherein at least one Z' on each Z'-substituted carbon atom is hydrogen.

5. The spirodilactam of claim 4 of the structure 2,7-diphenyl-3,8-dibutyl-2,7-diazaspiro[4.4]nonane-1,6-dione.

6. The spirodilactam of claim 4 of the structure 2,7-diphenyl-2,7-diazaspiro[4.4]nonane-1,6-dione.

* * * * *